United States Patent [19]
Taboada

[11] Patent Number: 5,223,718
[45] Date of Patent: Jun. 29, 1993

[54] METHOD AND APPARATUS FOR QUANTIFYING THERMAL OXIDATION TESTER TUBE DEPOSITS

[75] Inventor: John Taboada, San Antonio, Tex.
[73] Assignee: Alcor, Inc., San Antonio, Tex.
[21] Appl. No.: 927,820
[22] Filed: Aug. 10, 1992
[51] Int. Cl.[5] .............................. G01N 21/64
[52] U.S. Cl. .............................. 250/458.1; 250/459.1; 436/172
[58] Field of Search .............. 250/458.1, 459.1, 461.1; 422/82.08; 436/172

[56] References Cited

U.S. PATENT DOCUMENTS

| | | | |
|---|---|---|---|
| 3,705,014 | 12/1972 | Townsley | 356/447 |
| 4,802,762 | 2/1989 | Hill, Jr. | 356/318 |
| 4,841,156 | 6/1989 | May et al. | 250/461.1 |
| 4,866,283 | 9/1989 | Hill, Jr. | 250/461.2 |
| 5,001,353 | 3/1991 | Odake et al. | 250/459.1 |
| 5,101,658 | 4/1992 | Wilson, III et al. | 73/61.2 |

Primary Examiner—Carolyn E. Fields
Attorney, Agent, or Firm—Gunn, Lee & Miller

[57] ABSTRACT

A short wavelength light beam such as the blue/green emission lines of an argon-ion laser, is projected through a narrow slit into a chamber onto a metal tube of the kind typically used to receive deposits in fuel testing. The spuriously reflected light is absorbed into the interior chamber wall. The beam spot on the tube is imaged by a short focal length lens onto a photodetector such as a photomultiplier tube. The radiation passing to the detector is filtered to block out all radiation except that having a wave length longer than the incident light. By this means, fluorescence from the deposits on such metal tubes, induced by the incident light beam, is quantified and is used as a proportional indication of the deposit thickness. The metal tube is simultaneously rotated and translated to scan the entire tube and thereby obtain a map of the tube deposits in order to establish a test rating for the fuel.

5 Claims, 4 Drawing Sheets

METHOD AND APPARATUS FOR QUANTIFYING THERMAL OXIDATION TESTER TUBE DEPOSITS

BACKGROUND OF THE INVENTION

1. Field of The Invention

The present invention relates generally to methods and apparatus for the optical inspection of materials. The present invention relates more specifically to a method and apparatus for using laser induced fluorescence to quantitatively measure thin deposits on test surfaces used in thermal oxidation testing for fuels.

2. Background Information

Jet aircraft engines commonly use the fuel flowing in the engine as a coolant in the various heat exchanges used in the engine systems. The unusual high temperatures of the heat exchangers often result in the thermal breakdown of the fuel and the depositing of carbonaceous deposits on the heated surfaces. These deposits degrade the performance of the heat exchangers and can clog important fuel flow lines ultimately resulting in engine breakdown. Jet engine fuels vary in this tendency to create deposits, some having a higher tendency than others. To assure quality control in the industry, thermal oxidation stability tests have been developed for quantifying this characteristic of aircraft fuels.

The present standard thermal oxidation stability tests for jet fuels are defined by the American Society for Testing Material (ASTM) in method D-3241 which utilizes an apparatus based upon U.S. Pat. No. 3,670,561 (Hundere I patent) which disclosure is incorporated herein by reference. The apparatus defined by the Hundere I patent is improved upon by the apparatus disclosed in U.S. Pat. No. 5,101,658 (Hundere II patent) which disclosure is also incorporated herein by reference In the Hundere patents process, a thermal oxidation test heater tube (TOT heater tube), typically an aluminum cylinder, is heated to a specific temperature and fuel under test is flowed over it for a specified time. Carbonaceous deposits from on the heated tube during the test and the maximum thickness of such deposits is used as a measure of the tendency of the fuel to break down and leave these deposits.

The level of tube deposits are presently rated by either the Mark 8A Tube Deposit Rater (available from Alcor, Inc., 10130 Jones Maltsberger Road, P.O. Box 32516, San Antonio, Tex. 78284) or a Tuberater (available from Erdco Engineering Corp., 721 Custer Avenue, Evanston, Ill. 60202), and used in conjunction with the ASTM color standard No. 12-416600-00. In the visual technique of rating the test results, the procedure for measuring the deposits involves an individual visually comparing the deposits on the metal tube with the ASTM color standard. This visual comparison method has several problems. It is not uncommon for different test operators to select different color values and, therefore, arrive at different fuel ratings. The color standards differ in color from the typical tube deposit color and the tubes themselves are round while the color standard is on a flat substrate. All of these subjective factors, therefore, tend to confound the fuel rating It would be desirable to have a more objective means for quantifying the level of tube deposits and thereby for rating the fuels tested U.S. Pat. No. 3,705,014, issued to Townsley, discloses an objective optical method based upon the absorption of light by the tube deposits. The limitation of this invention lies in the difficulty of assessing the absorption of the lightly deposited tubes, grades 1 and 2.

U.S. Pat. No. 3,705,014, issued to Townsley, also discusses the use of light to quantify the deposits of interest on a thermal oxidation tester tube. The principle of operation of the Townsley apparatus, however, depends upon measuring the diminution of the light impinging on the test tube. Since the deposits are a very thin coating on the tube, having only very slight absorption, the method depends upon detecting a small change superimposed on a large optical signal. No mention is made in Townsley of applying fluorescence to this approach to overcome this problem of signal detection.

U.S. Pat. No. 4,866,283, issued to Hill, discloses an optical inspection system using laser induced luminescence to detect the quality of organic materials on food products. The Hill patent, method, and apparatus, however, incorporates and requires the use of complex spectrometer optics and circuitry to analyze the frequency and wave length of the induced fluorescence. Hill does not address the quantification of thin deposits of trace materials on metal surfaces.

U.S. Pat. No. 4,802,762, also issued to Hill, describes an optical inspection system for using laser induced luminescence to detect the deterioration of a polymer base material. Here again, however, the apparatus and method require the use of a spectrometer for accurate indications of the physical characteristics of the specimen. Hill does not address the art of quantifying thin deposits of carbonaceous materials such as are found in thermal oxidation tests. The Hill apparatus is intended to quantify changes in bulk samples.

SUMMARY OF THE INVENTION

It is, therefore, an object of the present invention to provide an apparatus and means for the objective, quantification of deposits formed in the thermal oxidation testing of fluids, specifically jet fuel.

It is another object of the present invention to provide an apparatus and method for the objective and automatic quantification of thermal oxidation tube deposits for the purpose of quantitatively grading the quality of the fluid being tested.

It is another object of the present invention to provide a method and apparatus for quantitatively determining the level of deposits formed while testing the thermal oxidation characteristics of fluid that does not rely upon the subjective measurement of such deposits by visual comparison with standard coloration samples.

It is another object of the present invention to provide an apparatus and method for quantifying tube deposits in tests for the thermal oxidation characteristics of fuels utilizing an automatic objective measurement of the fluorescence induced by light impinging upon the formed deposits.

It is another object of the present invention to provide an objective, quantitative map of the deposits formed on a tube test sample from thermal oxidation testing of fluids.

It is another object of the present invention to provide a method and apparatus for automatically determining a quantity of deposits on a thermal oxidation test sample and associating those deposits with their spacial position on the test sample.

In fulfillment of these and other objectives, the present invention provides an apparatus and method for directing a short wave length light beam such as the blue/green emission lines of an argon/ion laser through a narrow slit into a chamber onto a metal tube of the kind typically used to receive deposits in fuel testing. Specular reflected light off of the metal tube is absorbed into the interior chamber walls and a beam spot on the metal tube is imaged at a right angle by a short focal length lens onto a photo detector such as a photo multiplier tube. The radiation passing to the detector is filtered to block out all radiation except that having a wave length longer than the incident light. By this means, fluorescence from the deposits on such metal tubes, induced by the incident light beam is quantified and is used as a proportional indication of the deposit thickness. The metal tube is simultaneously rotated and translated by a step drive mechanism to scan the entire tube and thereby obtain a map of the tube deposits in order to establish a test rating for the fuel.

DESCRIPTION OF THE PREFERRED EMBODIMENT

Figure 1:
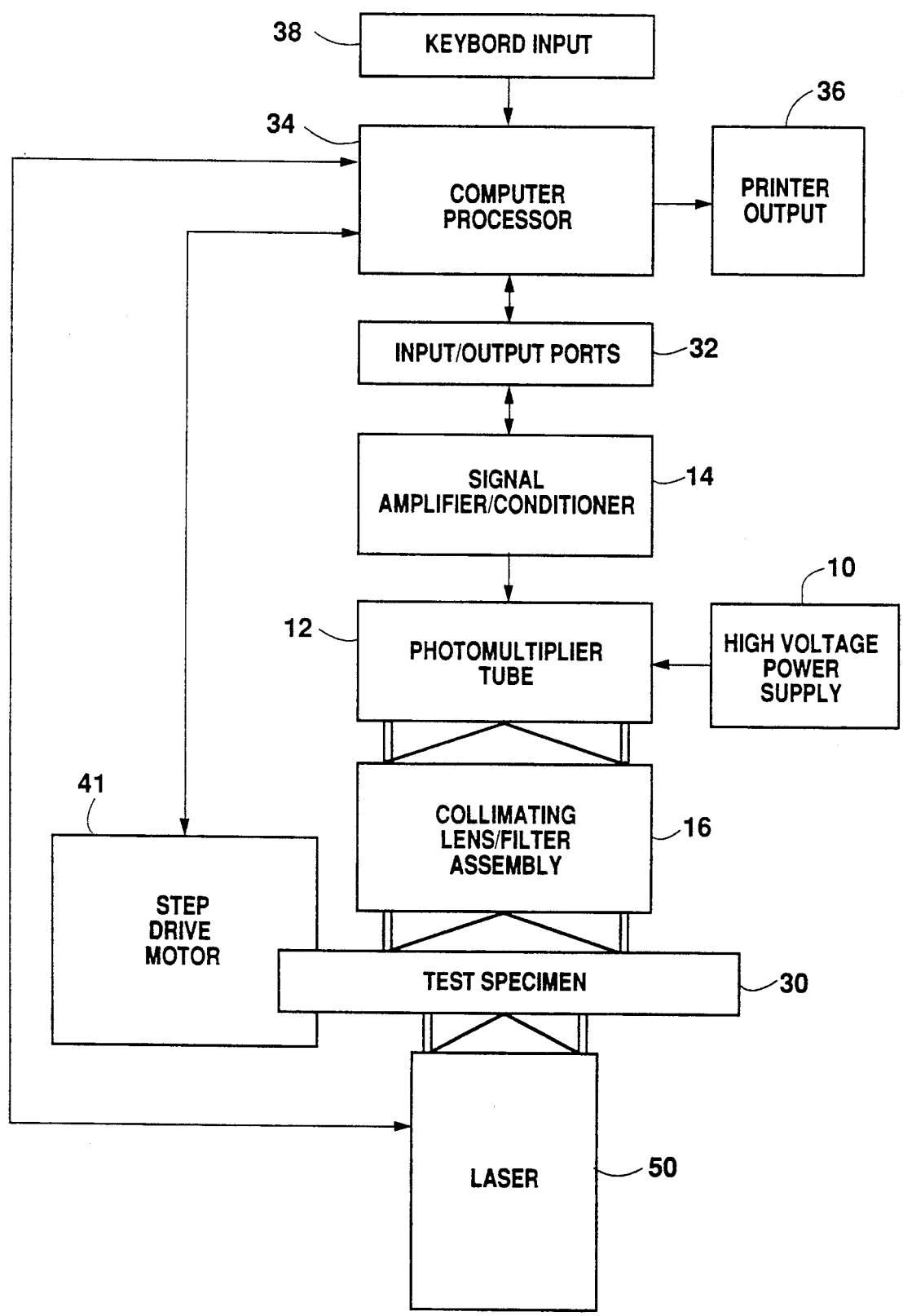
FIG. 1 is a block diagram of the general arrangement of the elements of the apparatus of the present invention.

Reference is first made to FIG. 1 for a detailed description of the arrangement of various discrete components within the overall system of the present invention.

Test specimen (30) which is typically a tubular metal coupon of the type described in the Hundere patent cited above is illuminated by laser (50) which in the preferred embodiment is an argon/ion laser that produces light in the blue/green wave lengths. Light from laser (50) impinges upon test specimen (30) according to a predetermined scan controlled by step drive motor (41). The specific apparatus for controlling the scan by way of step drive motor is described in more detail below. The light impinging upon test specimen (30) is both reflected and, to some extent absorbed by test specimen (30). That light energy which is absorbed by test specimen (30) induces fluorescence that emits additional light from test specimen (30), typically of a wave length longer than the incident blue/green light of the argon/ion laser. Collimating lens and filter assembly (16) filters and selects the light emitted from test specimen (30) that results from the fluorescence induced by the laser light from laser (50). The fluorescence emitted by test specimen (30) is typically caused by the polymers of tube deposits when these polymers absorb light of the frequencies incident thereon. The fluorescent emissions are imaged by collimating lens and filter assembly (16) and are focussed on photo multiplier tube (12). Photo multiplier tube (12) is powered by high voltage power supply (10) and provides an output signal to signal amplifier/conditioner (14). Signal amplifier/conditioner (14) provides an appropriate signal to input/output ports (32) associated with computer processor (34). Computer processor (34) is preprogrammed to receive an electronic signal from photo multiplier tube (12) by way of signal amplifier conditioner (14) and input/output ports (32) such that it may process the signal and identify characteristic amplitudes in the signal with predetermined standards for fluorescent emissions previously measured. Computer processor (34) is programmed by way of keyboard input (38) and by preprogrammed routines for the collection of data and the control of the test system that is provided to the test operator by way of printer output (36).

Computer processor (34) also controls the movement of test specimen (30) by way of its control of step drive motor (41). In this way, there is a constant correlation between the signal input from photo multiplier tube (12) and the position of test specimen (30) with respect to the laser light from laser (50) by way of computer processor (34) control of step drive motor (41). Computer processor (34) also provides the necessary on/off control of laser (50) in association with the automatic running of the test.

Figure 2:
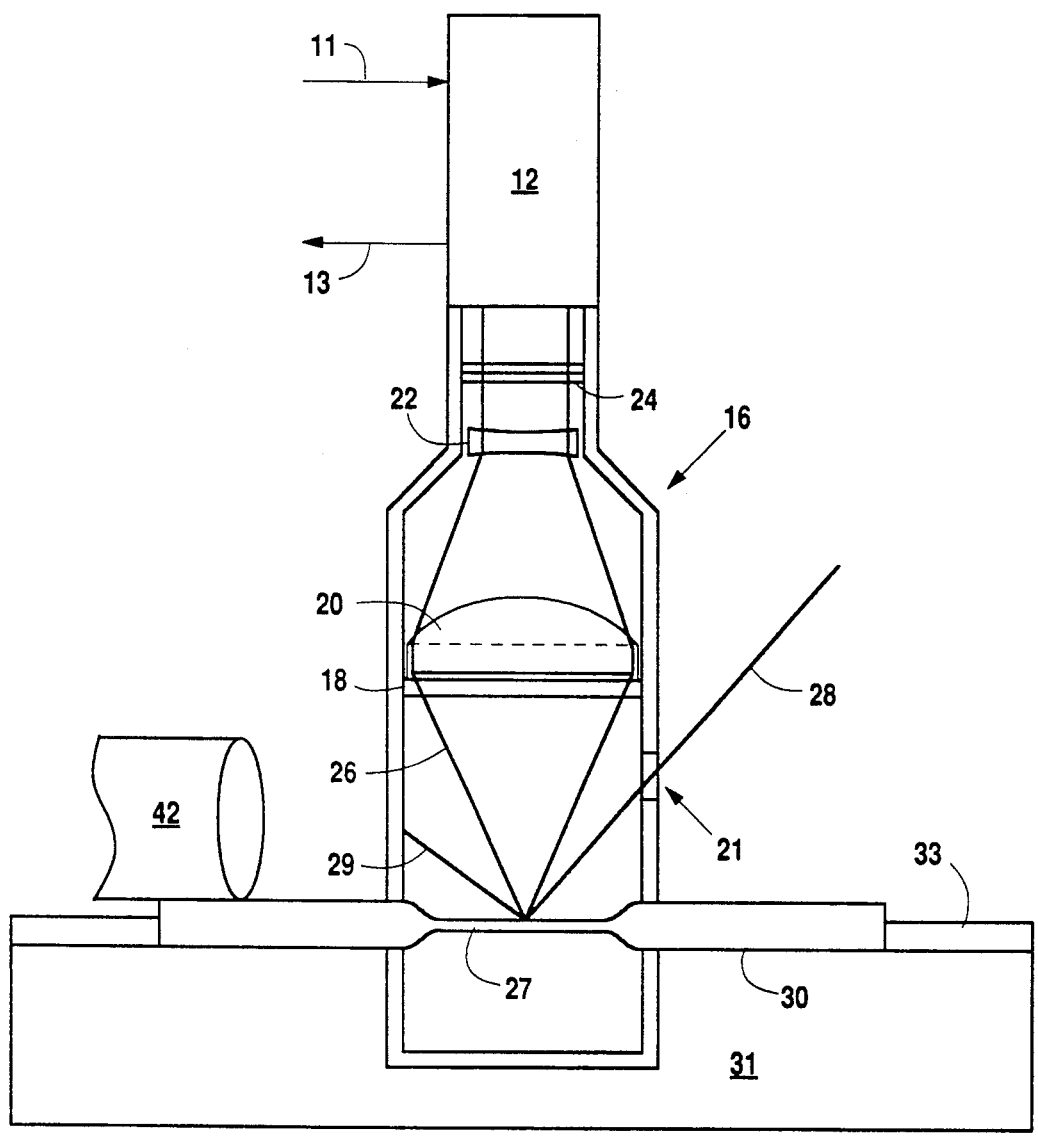
FIG. 2 is a cross-sectional view of the optical assembly and photo detector of the present invention.

Reference is now made to FIG. 2 for a more detailed description of a cross-sectional view of the imaging components of the apparatus of the present invention. Laser light (28) emitted from laser (50) (not shown) passes through slit (21) located on one side of otherwise light tight enclosure (16). Laser beam (28) impinges upon a top side of test specimen (30) in an area (27) associated with the deposits of carbonaceous material as a result of a typical test run described by the Hundere patent apparatus. Most of the light reflected (29) from test specimen (30) is absorbed by the blackened inner walls of enclosure (16). The fluorescent emissions (26), which are generally of a wave length longer than the reflected light (29), are imaged by positive lens (20) onto collimating lens (22). The fluorescent emissions (26) are induced by laser light (28) impinging upon the polymers of the tube deposits on test specimen (30) and is separated from the reflected light (29) by way of filters (18) and (24). Filters (18) and (24), in order to filter out light found in the blue/green wave length typical of argon/ion lasers, are usually orange in color. Filter (24) may be a dichromic filter.

The optical system comprising positive lens (20) and collimating lens (22) collimates the fluorescent light as it leaves lens (22). Fluorescent emission (26) is then collected by photo multiplier tube (12).

Photo multiplier tube (12) is powered by high voltage power supply (10) (not shown) along conductor (11). A signal is provided from photo multiplier tube along conductor (13) to signal amplifier conditioner (14) (not shown).

Figure 3:
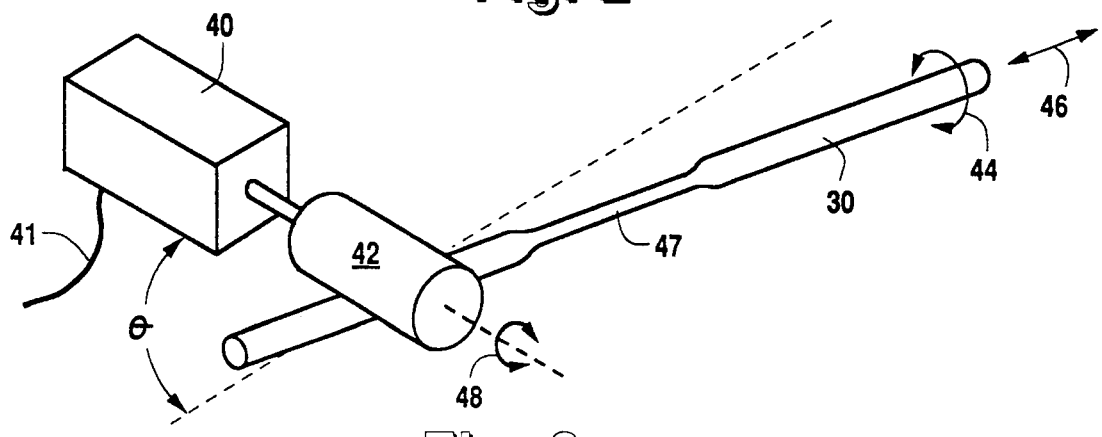
FIG. 3 is a perspective view of the means for automatic rotation and translation of the test specimen tube in the apparatus of the present invention.

Reference is now made to FIG. 3 for a detailed description of the method of controlling the scan of laser beam (28) on test specimen (30). In FIG. 3, step drive motor (40) is shown to control and rotate rubberized cylinder (42) in accordance with preprogrammed steps designed to scan laser beam (28) (not shown) across test specimen (30). Stepping motor (40) is controlled by computer processor (34) (not shown) by way of conductor (41). Rubberized cylinder (42) is spring loaded against test specimen (30) so as to maintain a constant contact in pressure with test specimen (30). The axis of rotation of cylinder (42) is aligned at a slight angle to the alignment of test specimen (30) which is confined to ride in grove (33) located on base plate (31) shown better in FIG. 4. The combination of the rotation of rubberized cylinder (42) and its angle with respect to the axis of test specimen (30) create both a coordinated rotational motion to test specimen (30) shown at (44) and a translational motion of test specimen (30) shown as motion (46). The rotation of stepping motor (40) and its control of rubberized cylinder (42) can be made in either direction as shown in (48) so as to rotate and translate test specimen (30) in a spiral motion. In this matter, deposit area (47) is moved completely under the scan of laser beam (28) (not shown).

Figure 4:
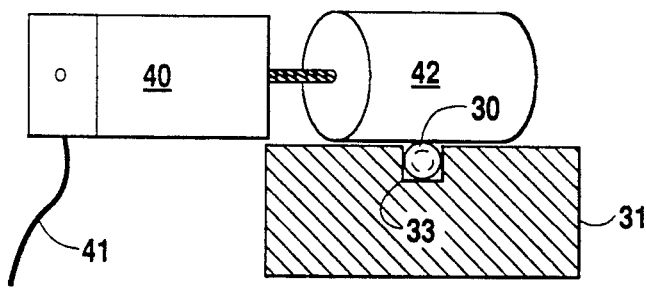
FIG. 4 is a partial cross-sectional end view of the means for automatic rotation and translation of the test specimen shown in FIG. 3.

Reference is now made to FIG. 4 for a detailed description of an end view of the apparatus described above with respect to FIG. 3. In FIG. 4, stepping motor (40), which is controlled by computer processor (34) (not shown) by way of conductor (41), controls the rotational motion of rubberized cylinder (42) in accordance with preprogrammed steps. Rubberized cylinder (42) is in contact with test specimen (30) which rides in grove (33) formed in base plate (31). In the view shown in FIG. 4, test specimen (30) is seen along its axis and rotates within grove (33) and moves along grove (30) as it is drawn by the rotation of rubberized cylinder (42). In this manner, as described above, the entire region to be scanned (47) is spirally drawn through the path of laser beam (28) (not shown).

Figure 5:
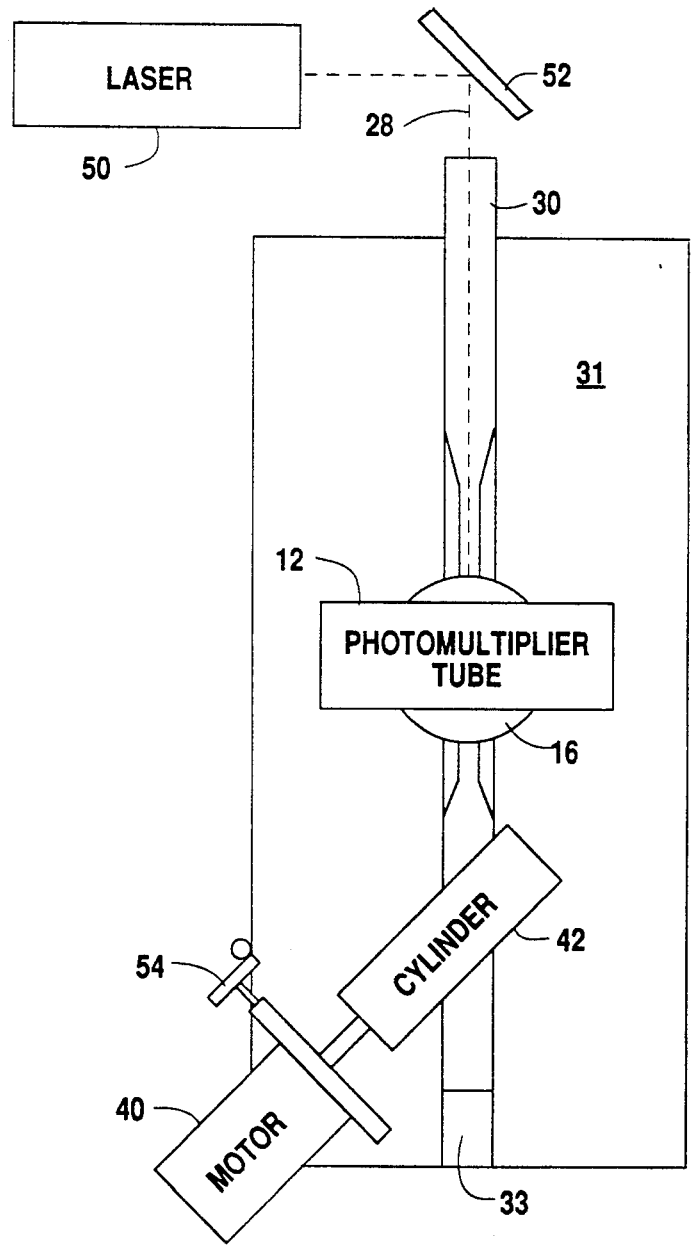
FIG. 5 is a top view of the apparatus of the present invention.

Reference is now made to FIG. 5 for a top view of the entire assembly of the apparatus of the present invention. It is particularly noted that stepping motor (40) is pivotally mounted at point (54) to base plate (31) and spring loaded (not shown) so as to keep rubberized cylinder (42) in contact with test specimen (30). Pivot point (54) is adjustable so as to vary the rate at which the translation of test specimen (30) occurs with respect to its rotation. At one extreme wherein rubberized cylinder (42) is at right angles to test specimen (30), there is little or no rotation with only transnational motion of test specimen (30). The closer rubberized cylinder (42) and test specimen (30) are to being parallel in their axis the more rotations per translational distance unit are achieved. In this manner, a more or less detailed map of the scan area described above can be obtained.

In FIG. 5, laser beam (50) is shown directing laser beam (28) at targeting mirror (52) which directs laser beam (28) further through slit (not shown) in enclosure (16) where it impinges upon the target area of test specimen (30). Photo multiplier tube (12) is shown in its position atop optical assembly (16) where it collects the light created by the luminescence effected by the carbonaceous deposits found on test specimen (30).

Figure 6:
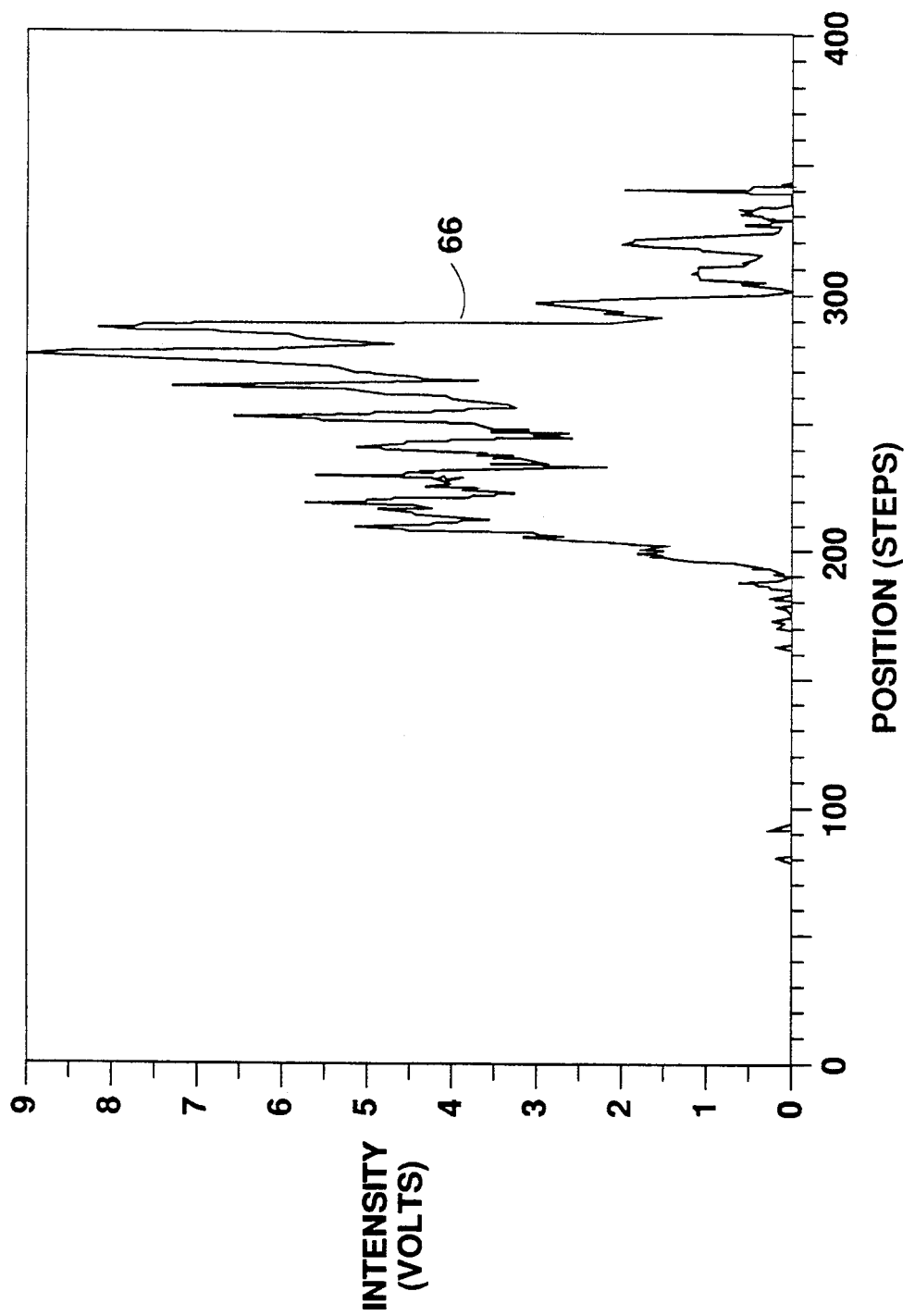
FIG. 6 is a graphic depiction of a typical scan data obtained from the method and apparatus of the present invention.

Reference is now made to FIG. 6 for a typical output from the apparatus of the present invention showing the means whereby deposits on test specimen (30) may be quantitatively analyzed. Curve (66) in the graph represents the intensity of the fluorescence from test specimen (30) as it is rotationally and translationally scanned. Position indications shown on the "X" axis of the graph shown in FIG. 6 may be correlated with the controlled step drive motor (40) and associated with a particular intensity by way of computer processor (34). The periodic spikes in curve (66) indicate that the deposits are not consistently distributed about the tube, but rather occur at times along one side of the test specimen (30) or in patches on the surface of test specimen (30). Curve (66) can be compared to standardized curves for various known quantities of deposits on test specimen (30) and a quantitative value for the level of deposits can be determined. This quantitative level of a value of deposits can be associated with the parameters run by the test as described in the Hundere patent cited above. The combination of the measure of deposits and the parameters of the test can provide an objective means whereby a fuel rating can be described to the fuel under test.

Reference is again made to FIG. 2 for a description of the method of implementing the apparatus of the present invention so as to effect an automatic, objective analysis of the deposits formed on test specimen (30).

Test specimen (30) may be slid into grove (33) in base plate (31) through appropriate apertures in enclosure (16) and under rubberized cylinder (42). Test specimen (30) may be initially positioned so as an upper section of scan area (47) (shown in FIG. 3) is positioned to receive the incident laser beam light (28) through slit (21) and enclosure (16). Step drive motor (40) is controlled by computer processor (34) so as to gradually rotate and draw test specimen (30) through the appropriately positioned apertures in enclosure (16). At an appropriate point in the controlled positioning of test specimen (30), laser beam light (20) is turned on and illuminates a target area on test specimen (30). Reflected light is absorbed with enclosure (16) and appropriate luminescent light is collected and filtered and collimated to photo multiplier tube (12). Photo multiplier tube (12) provides a constant amplitude value to computer processor (34) by way of signal amplifier/conditioner (14) and input/output ports (32). Computer processor (34) constantly correlates the amplitude of the signal received from photo multiplier tube (12) with the position known from its control of step drive motor (40). The position known by its control of step drive motor (40) is stored in an array associated with the amplitude of the signal received. In this way, a graph of the form shown in FIG. 6 can be generated by computer processor (34) and presented at printer output (36). A graph of the type shown in FIG. 6 can be compared to a standard graph with known deposition characteristics and a quantitative value assigned to the deposition tendencies of the fuel having been tested. In this manner, a fuel rating can be assigned to the fuel being tested that is objectively indicative of its tendency to form deposits in the presence of high temperature thermal oxidation.

Although the present invention has hereinabove been described with reference to specific embodiments, this description is not intended to be construed in a limiting sense. A number of various modifications of the preferred embodiment, as well as alternative embodiments of the invention, will become apparent to persons skilled in the art upon reference to the description of the invention and to the appended claims. It is, therefore, contemplated that the appended claims will cover such modifications that fall within the scope of the invention.

I claim:

1. An apparatus for quantifying a level of deposits on a test specimen utilized in liquid fuel thermal oxidation test devices, comprising:
   means for illuminating said test specimen with light, said light having a first wave length predetermined to induce fluorescent radiation having a second wave length, when said deposits are illuminated by said light;
   means for selecting the induced fluorescent radiation from said light and directing said fluorescent radiation away from said test specimen;
   means for measuring a level of said fluorescent radiation emitted from said deposits on said test specimen;

means for correlating said fluorescent radiation level with a known position on said test specimen and, creating an array of data elements based upon the correlation; and means for comparing said array of data elements with a known array of data elements previously determined to be indicative of given levels of deposits on said test specimen, wherein by unknown levels of deposits are quantified and are determined to be indicative of an objective test fuel rating.

2. The apparatus according to claim 1, wherein said means for correlating a level of said fluorescent radiation with a known position of said test specimen comprises:

means for rotating said test specimen; and means for translating said test specimen beneath said light in a coordinating spiral motion.

3. The apparatus according to claim 1, wherein said means for measuring said fluorescent radiation is a photo multiplier tube.

4. The apparatus according to claim 1, wherein, said means for correlating said fluorescent radiation level with said known position on said test specimen further comprises a computer processor capable of collecting and storing both said fluorescent radiation level and position information for a plurality of points on said test specimen.

5. A method for the optical inspection of a test specimen of the type used to collect deposits in thermal oxidation fuel testing comprising the steps of:

directing light of a first wave length at a scan area on said test specimen, said scan area known to contain said deposits resulting from said thermal oxidation fuel testing;

inducing fluorescent radiation from said deposits by directing said light on said deposits;

collimating said fluorescent radiation and filtering said fluorescent radiation from said light;

measuring an amplitude value of said fluorescent radiation;

correlating said amplitude value of said fluorescent radiation with a known position of said light on said test specimen;

storing a plurality of correlated fluorescent radiation amplitudes and known positions thereby creating a map of fluorescent radiation characteristics of said test specimen; and comparing said plurality of correlated fluorescent radiation amplitudes and known positions with predetermined standard information regarding known deposit characteristics.

* * * * *